US009903868B2

(12) United States Patent
Chen et al.

(10) Patent No.: US 9,903,868 B2
(45) Date of Patent: Feb. 27, 2018

(54) METHOD FOR THE DETECTION AND QUANTITATION OF BIOMARKERS

(71) Applicant: The United States of America, as represented by the Secretary, Department of Health and Human Services, Washington, DC (US)

(72) Inventors: Xiaoyuan Chen, Potomac, MD (US); Dingbin Liu, Tianjin (CN)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/714,721

(22) Filed: May 18, 2015

(65) Prior Publication Data

US 2015/0330976 A1    Nov. 19, 2015

Related U.S. Application Data

(60) Provisional application No. 61/994,622, filed on May 16, 2014, provisional application No. 62/052,866, filed on Sep. 19, 2014.

(51) Int. Cl.
| | |
|---|---|
| *G01N 33/574* | (2006.01) |
| *C12Q 1/26* | (2006.01) |
| *G01N 33/58* | (2006.01) |
| *G01N 33/543* | (2006.01) |

(52) U.S. Cl.
CPC ......... *G01N 33/57434* (2013.01); *C12Q 1/26* (2013.01); *G01N 33/543* (2013.01); *G01N 33/587* (2013.01)

(58) Field of Classification Search
None
See application file for complete search history.

(56) References Cited

U.S. PATENT DOCUMENTS

| 4,816,567 A | 3/1989 | Cabilly et al. | |
|---|---|---|---|
| 5,807,978 A * | 9/1998 | Kokolus | G01N 33/57434 424/184.1 |
| 6,300,064 B1 | 10/2001 | Knappik et al. | |
| 7,951,554 B2 | 5/2011 | Hainfeld et al. | |
| 2003/0108555 A1* | 6/2003 | Marinkovich | A61K 38/19 424/178.1 |
| 2008/0160634 A1* | 7/2008 | Su | G01N 27/745 436/501 |
| 2009/0117574 A1 | 5/2009 | Labgold et al. | |
| 2010/0093557 A1 | 4/2010 | Kumble | |
| 2012/0202217 A1 | 8/2012 | Adamczyk et al. | |
| 2013/0115604 A1 | 5/2013 | Watson et al. | |
| 2013/0189287 A1* | 7/2013 | Bregeon | A61K 47/48215 424/180.1 |

FOREIGN PATENT DOCUMENTS

| WO | WO 2006/008742 A1 * | 1/2006 | ............... C12Q 1/26 |
|---|---|---|---|
| WO | WO 2014/020293 A1 | 2/2014 | |

OTHER PUBLICATIONS de la Rica & Stevens (Nature Protocols Aug. 22, 2013 1759-1764).*
Debets et al. (Chem. Commun. 2010, 46:97-99).*
Kouassi et al. (BioMagnetic Res. Tech. Mar. 11, 2005 3:1 doi:10.1186/1477-044X-3-1).*
National Honey Board (http://www.honey.com/images/downloads/carb.pdf, Dec. 23, 2016).*
Chen et al., "Simultaneous determination of human Enterovirus 71 and Coxsackievirus B3 by dual-color quantum dots and homogeneous immunoassay," *Anal. Chem.*, 84 (7), 3200-3207 (2012).
De La Rica et al., "Plasmonic ELISA for the ultrasensitive detection of disease biomarkers with the naked eye," *Nat. Nanotechol.*, 7 (12), 821-824 (2012).
Eom et al., "Adenosine Triphosphate (ATP)-Stabilized Gold Nanoparticle Based-colorimetric Acetylcholinesterase Assay Method with High Signal/Noise Ratio in End-point Analysis," *Bull. Korean Chem. Soc.*, 32 (1), 329-331 (2011).
Gao et al., "Magnetic bead-based reverse colorimetric immunoassay strategy for sensing biomolecules," *Anal. Chem.*, 85 (14), 6945-6952 (2013).
Knappik et al., "Fully synthetic human combinatorial antibody libraries (HuCAL) based on modular consensus frameworks and CDRs randomized with trinucleotides," *J. Mol. Biol.*, 296 (1), 57-86 (2000).
Köhler et al., "Derivation of specific antibody-producing tissue culture and tumor lines by cell fusion," *Eur. J. Immunol.*, 6 (7), 511-519 (1976).
Krebs et al., "High-throughput generation and engineering of recombinant human antibodies," J. Immunol. Methods, 254, 67-84 (2001).
Krishnan et al., "Attomolar detection of a cancer biomarker protein in serum by surface plasmon resonance using superparamagnetic particle labels," *Angew. Chem. Int. Ed. Engl.*, 50 (5), 1175-1178 (2011).

(Continued)

*Primary Examiner* — Peter J Reddig
(74) *Attorney, Agent, or Firm* — Leydig, Voit & Mayer, Ltd.

(57) ABSTRACT

The invention provides a method for detecting the presence or absence of a biomarker in a biological sample at a very low concentration comprising the steps of (a) contacting the biological sample with a capture binding sequence immobilized on a surface, (b) providing a conjugate comprising a detection binding sequence-glucose oxidase, (c) contacting the surface with the detection binding sequence-glucose oxidase conjugate, (d) separating any unbound detection binding sequence-glucose oxidase conjugate from the surface, (e) incubating the resulting surface with a glucose solution and a mixture comprising gold nanoparticles and a gold salt, wherein the gold nanoparticles have an initial particle size of about 5 nm, and (f) observing any change in color of the mixture. The invention also provides a method for diagnosing the presence of a prostate cancer biomarker in a subject and a kit for detecting or quantifying a biomarker in a biological sample.

12 Claims, 8 Drawing Sheets

(56) References Cited

OTHER PUBLICATIONS

Liu et al., "Acetylcholinesterase-catalyzed hydrolysis allows ultrasensitive detection of pathogens with the naked eye," *Angew. Chem. Int. Ed. Engl.*, 52 (52), 14065-14069 (2013).

Thaxton et al., "Nanoparticle-based bio-barcode assay redefines "undetectable" PSA and biochemical recurrence after radical prostatectomy," *Proc Natl. Acad. Sci. U.S.A.*, 106 (44), 18437-18442 (2009).

Wu et al., "Simultaneous detection of enterovirus 71 and coxsackievirus A16 using dual-colour upconversion luminescent nanoparticles as labels," *Chem. Commun.*, 48 (40), 4866-4868 (2012).

Zayats et al., "Biocatalytic growth of Au nanoparticles: from mechanistic aspects to biosensors design," *Nano Lett.*, 5 (1), 21-25 (2005).

\* cited by examiner

METHOD FOR THE DETECTION AND QUANTITATION OF BIOMARKERS

CROSS-REFERENCE TO RELATED APPLICATIONS

This patent application claims the benefit of U.S. Provisional Patent Applications No. 61/994,622, filed May 16, 2014, and 62/052,866, filed Sep. 19, 2014, which are incorporated by reference.

BACKGROUND OF THE INVENTION

Ultrasensitive quantification of cancer biomarkers in complex samples is of great significance to clinical decision-making, and thus facilitates enabling early-stage diagnosis, monitoring cancer progression and evaluating therapeutic interventions. Currently available quantitative immunoassays, such as enzyme-linked immunosorbent assay (ELISA), the most popular format in clinical biomarker detection, typically measure protein biomarkers at concentrations above 0.1 ng/mL (Thaxton, C. S. et al., *Proc. Natl. Acad. Sci. U.S.A.* 2009, 106: 18437-18442). This detection sensitivity is unable to reach the clinical threshold of many protein biomarkers especially in the early stages of the diseases when their concentrations in clinical samples are generally in the range of fg/mL to pg/mL. It is therefore extremely important to develop quantitative immunoassays with ultra high sensitivity.

The past decades have witnessed a variety of enhanced immunoassays with ultrahigh sensitivity. Amongst these strategies, gold nanoparticle (AuNP)-based colorimetric assays have been incorporated with immunoreactions for biomarker detection, which have drawn considerable attention owing to their unprecedented sensitivity and convenient readout. Presently, AuNP-based colorimetric assays mainly depend on the monodisperse or aggregated process of AuNPs, where detection target-induced molecular events are transformed into the respective red-to-blue (or purple) color change. These clear red-to-blue (or purple) results can be easily distinguished by the naked eye, making it suitable for point-of-care (POC) diagnostics. Although the reported AuNP-based immunoassays provide sufficiently high sensitivity, most of them are unable to quantify the detection targets of interest due to their narrow linear detection ranges.

Thus, there exists an unmet need for an ultrasensitive and quantitative immunoassay.

BRIEF SUMMARY OF THE INVENTION

The invention provides a method for detecting the presence or absence of a biomarker in a biological sample comprising the steps of (a) contacting the biological sample with a capture binding sequence immobilized on a surface, (b) providing a conjugate comprising a detection binding sequence-glucose oxidase, (c) contacting the surface with the detection binding sequence-glucose oxidase conjugate, (d) separating any unbound detection binding sequence-glucose oxidase conjugate from the surface, (e) incubating the resulting surface with a glucose solution and a mixture comprising gold nanoparticles and a gold salt, wherein the gold nanoparticles have an initial particle size of about 5 nm, and (f) observing any change in color of the mixture.

The invention also provides a method for diagnosing the presence of a prostate cancer biomarker in a subject comprising the steps of (a) contacting a biological sample obtained from the subject with a capture antibody immobilized on a surface, (b) providing magnetic beads having a detection antibody and glucose oxidase conjugated thereto, (c) contacting the surface with the magnetic beads, (d) separating any unbound magnetic beads from the surface, (e) incubating the resulting surface with a glucose solution and a mixture comprising gold nanoparticles and a gold salt, wherein the gold nanoparticles have an initial particle size of about 5 nm, and (f) observing any change in color of the mixture.

The invention further provides a kit for detecting or quantifying a biomarker in a biological sample comprising (a) a solid phase comprising a capture binding sequence immobilized on a surface of the solid phase, (b) a detection binding sequence-glucose oxidase conjugate, (c) a glucose solution, and (d) a mixture comprising gold nanoparticles and a gold salt, wherein the gold nanoparticles have an initial particle size of about 5 nm.

Advantageously, the inventive method exhibits a limit of detection in the attomolar range, which exceeds that of commercial enzyme-linked immunosorbent assays ("ELISA") by more the 4 orders of magnitude. The inventive method further exhibits a linear detection range from 10 to $10^5$ fg/mL. The inventive method additionally provides a colorless-to-red color change which is easily distinguished by the naked eye, which is particularly suitable for use in point-of-care diagnostics.

BRIEF DESCRIPTION OF THE SEVERAL VIEWS OF THE DRAWING(S)

FIG. 1 depicts the absorbance exhibited by a mixture of 5 nm gold nanoparticles (8.3 nM) in the presence of various concentrations of $H_2O_2$ and $HAuCl_4$ (0.6 nM). The inset depicts the region between 0 μM and 100 μM of $H_2O_2$.

FIGS. 2A-D depict TEM images of 5 nm gold nanoparticles (FIG. 2A) and after addition of 10 μM of $H_2O_2$ (FIG. 2B), 100 μM of $H_2O_2$ (FIG. 2C), and 1000 μM of $H_2O_2$ (FIG. 2D).

FIGS. 3A-D depict dynamic light scattering (DLS) analysis of 5 nm gold nanoparticle seeds (FIG. 3A) and those in the presence of $HAuCl_4$ (0.6 mM) and 10 (FIG. 3B), 100 (FIG. 3C), and 1000 (FIG. 3D) μM of $H_2O_2$ respectively.

DETAILED DESCRIPTION OF THE INVENTION

Figure 1:
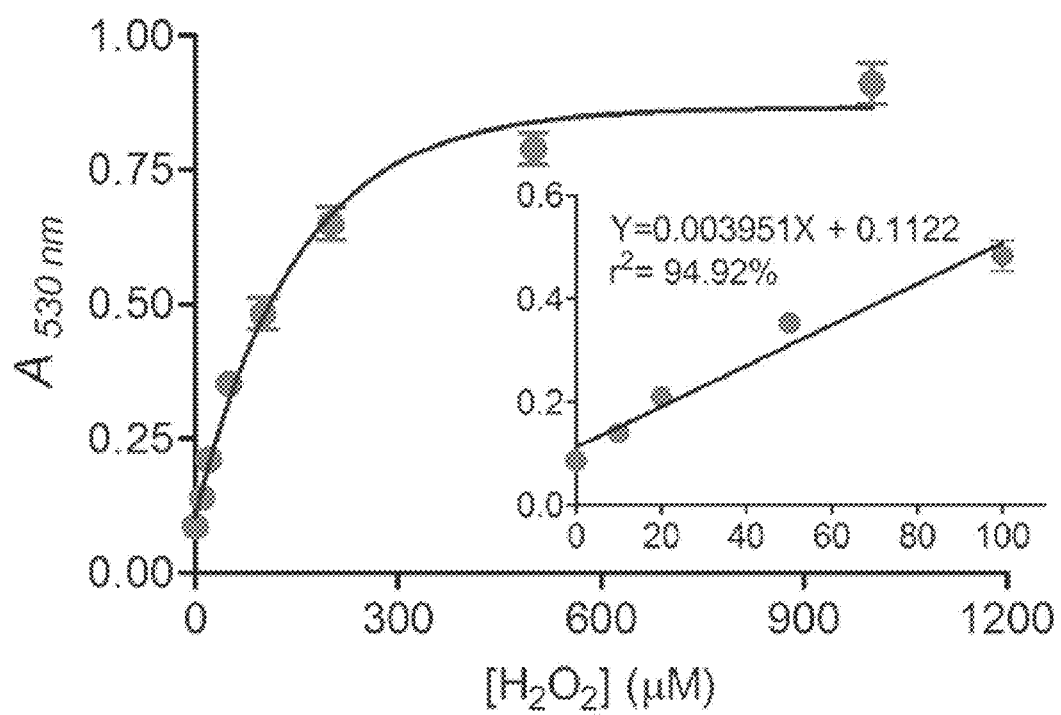

The invention provides a method for detecting the presence or absence of a biomarker in a biological sample comprising the steps of (a) contacting the biological sample with a capture binding sequence immobilized on a surface, (b) providing a conjugate comprising a detection binding sequence-glucose oxidase, (c) contacting the surface with the detection binding sequence-glucose oxidase conjugate, (d) separating any unbound detection binding sequence-glucose oxidase conjugate from the surface, (e) incubating the resulting surface with a glucose solution and a mixture comprising gold nanoparticles and a gold salt, wherein the gold nanoparticles have an initial particle size of about 5 nm, and (f) observing any change in color of the mixture.

As used herein, the term "biomarker" of a disease or condition refers to a gene or a gene product that is up- or down-regulated in a biological sample of a subject having the disease or condition relative to a biological sample from like tissue derivation, which gene or gene product is sufficiently specific to the disease or condition that it can be used, optionally with other genes or gene products, to identify or detect the disease or condition. Generally, a biomarker is a gene or a gene product that is characteristic of the disease or condition.

In an embodiment, the biomarker is a cancer biomarker. The cancer biomarker can be any suitable biomarker that is associated with a particular cancer. In a preferred embodiment, the cancer biomarker is a prostate cancer biomarker. Examples of suitable prostate cancer biomarkers include, for example, those described in US Patent Application Publication No. US 2013/0115604 A1, the disclosure of which is incorporated herein totally by reference. In a more preferred embodiment, the cancer biomarker is prostate specific antigen ("PSA").

The capture binding sequence is immobilized on a surface. The surface can be any suitable surface and is typically the surface of a suitable substrate. Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene fluoride, polyester, cellulose acetate, mixed cellulose esters, and polycarbonate. Suitable microporous membranes include, for example, those described in US Patent Application Publication No. US 2010/0093557 A1.

The capture binding sequence can be any suitable binding sequence that binds to a cancer biomarker of interest. The capture binding sequence can be an antibody, a protein, a peptide, an aptamer, and the like. In a preferred embodiment, the capture binding sequence is an antibody. The capture binding sequence can be an "antigen-binding fragment" of an antibody, which refers to the part of the antibody that participates in antigen binding. The antigen binding site is formed by amino acid residues of the N-terminal variable ("V") regions of the heavy ("H") and light ("L") chains.

Antibodies may be prepared by any of a variety of techniques known to those of ordinary skill in the art (see, for example, Harlow and Lane, Antibodies: A Laboratory Manual, Cold Spring Harbor Laboratory, 1988). Antibodies can be produced by cell culture techniques, including the generation of monoclonal antibodies as described herein, or via transfection of antibody genes into suitable bacterial or mammalian cell hosts, in order to allow for the production of recombinant antibodies.

In a preferred embodiment, the capture binding sequence is a monoclonal primary anti-human PSA antibody. Monoclonal antibodies may be prepared using hybridoma methods, such as the technique of Kohler and Milstein (*Eur. J. Immunol.* 1976, 6: 511-519), and improvements thereto. These methods involve the preparation of immortal cell lines capable of producing antibodies having the desired specificity. Monoclonal antibodies may also be made by recombinant DNA methods, such as those described in U.S. Pat. No. 4,816,567. DNA encoding antibodies employed in the disclosed methods may be isolated and sequenced using conventional procedures. Recombinant antibodies, antibody fragments, and/or fusions thereof, can be expressed in vitro or in prokaryotic cells such as bacteria, or eukaryotic cells such as yeast, insect or mammalian cells and further purified as necessary using methods that are well known in the art.

Antibodies may also be derived from a recombinant antibody library that is based on amino acid sequences that have been designed in silico and encoded by polynucleotides that are synthetically generated. Methods for designing and obtaining in silico-created sequences are known in the art (Knappik et al., 2000, *J. Mol. Biol.* 296: 254:57-86; Krebs et al., *J. Immunol. Methods* 2001, 254: 67-84, 2001; U.S. Pat. No. 6,300,064).

The conjugate comprising a detection binding sequence-glucose oxidase is a detection binding sequence conjugated to glucose oxidase ("GOx"). The detection binding sequence can be any suitable detection binding sequence that can bind to the biomarker of interest. The detection binding sequence can be an antibody, a protein, a peptide, an aptamer, and the like. In a preferred embodiment, the detection binding sequence is an antibody. The detection antibody can be as described herein for the capture antibody. In a preferred embodiment, the detection binding sequence is a secondary anti-human PSA antibody.

In an embodiment, the detection binding sequence is a dibenzocyclooctyl-conjugated binding sequence, for example, a dibenzocyclooctyl-conjugated antibody (e.g., a dibenzocyclooctyl-conjugated secondary anti-human PSA antibody).

The detection binding sequence can be conjugated to dibenzocyclooctyne, for example, by combining the detection binding sequence with NHS-activated dibenzocyclooctyne. The product can be purified, for example, using a centrifugal filter device. After preparation of the dibenzocyclooctyl-conjugated binding sequence, the dibenzocyclooctyl-conjugated binding sequence can be conjugated with glucose oxide, for example, by modifying the glucose oxidase with azide groups using, for example, NHS-activated azide.

In a preferred embodiment, the detection binding sequence-glucose oxidase conjugate is further conjugated to a nanoparticle or microparticle. Non-limiting examples of suitable nanoparticles and microparticles include polystyrene beads or magnetic beads. In this embodiment, the detection binding sequence can be conjugated with dibenzocyclooctyne. The nanoparticle or microparticle, for example, magnetic beads, can be conjugated with glucose oxidase. The glucose oxidase-conjugated nanoparticle or microparticle can then be conjugated with the benzocyclooctyl-conjugated binding sequence.

In an embodiment of the inventive method, a biological sample obtained from a subject is contacted with the capture binding sequence immobilized on a surface. A biomarker, if present, can bind to the capture binding sequence. The surface is contacted with the detection binding sequence-glucose oxidase conjugate. The detection binding sequence-glucose oxidase conjugate can bind to the biomarker, if present, thus the captured biomarker pulls down the detection binding sequence-glucose oxidase conjugate to the surface. A separation step is performed to separate any unbound detection binding sequence-glucose oxidase conjugate from the surface. The resulting surface is then incubated with a glucose solution and a mixture comprising gold nanoparticles and a gold salt, wherein the gold nanoparticles have an initial particle size of about 5 nm.

The mixture comprising gold nanoparticles and a gold salt can comprise any suitable gold salt. Non-limiting examples of suitable gold salts include salts of $HAuCl_4$.

When a biomarker is present and captured by the capture binding sequence, the glucose oxidase which is conjugated to the detection binding sequence reacts with glucose to form hydrogen peroxide. The hydrogen peroxide causes growth of the gold nanoparticles to a size of approximately 30 nm. The mixture comprising gold nanoparticles having a particle size of about 5 nm and the gold salt is substantially colorless. Upon growth of the gold nanoparticles, the mixture absorbs visible light at a wavelength of approximately 530 nm, such that the mixture develops a red-to-purple color which can be detected visually or spectrophotometrically.

Desirably, the inventive method has a linear detection range of from 10 to $10^5$ fg/mL of biomarker.

The invention also provides a method for diagnosing a presence of prostate cancer in a subject comprising the steps of (a) contacting a biological sample obtained from the subject with a capture antibody immobilized on a surface, (b) providing magnetic beads having a detection antibody and glucose oxidase conjugated thereto, (c) contacting the surface with the magnetic beads, (d) separating any unbound magnetic beads from the surface, (e) incubating the resulting surface with a glucose solution and a mixture comprising gold nanoparticles and a gold salt, wherein the gold nanoparticles have an initial particle size of about 5 nm, and (f) observing any change in color of the mixture. The capture antibody, the surface, the magnetic beads, the detection antibody conjugated with glucose oxidase, can be as described herein.

In a particular embodiment, the method for diagnosing the presence of a prostate cancer biomarker in a subject comprises the steps of (a) contacting a biological sample obtained from the subject with a capture antibody, wherein the capture antibody is a mouse monoclonal antibody to human prostate specific antigen, and which antibody is the CHYH1 clone, wherein the capture antibody is immobilized on a polystyrene surface, (b) providing magnetic beads having a detection antibody and glucose oxidase conjugated thereto, wherein the detection antibody is a mouse monoclonal antibody to human prostate specific antigen, and which antibody is the CHYH2 clone, (c) contacting the surface with the magnetic beads, (d) separating any unbound magnetic beads from the surface, (e) incubating the resulting surface with a glucose solution and an aqueous mixture comprising gold nanoparticles and gold (III) chloride trihydrate, wherein the gold nanoparticles have an initial particle size of about 5 nm, and (f) observing any change in color of the mixture As used herein, a "subject" is a mammal, e.g., a human, mouse, rat, guinea pig, dog, cat, horse, cow, pig, or non-human primate, such as a monkey, chimpanzee, baboon or rhesus.

The invention further provides a kit for detecting or quantifying a cancer biomarker in a biological sample comprising (a) a solid phase comprising a capture binding sequence immobilized on a surface of the solid phase, (b) a detection binding sequence-glucose oxidase conjugate, (c) a glucose solution, and (d) a mixture comprising gold nanoparticles and a gold salt, wherein the gold nanoparticles have an initial particle size of about 5 nm.

The inventive method described herein can be used to diagnose many types of diseases or disorders.

In particular instances, the inventive method can be used to diagnose hyperproliferative, hyperplastic, metaplastic, dysplastic, or pre-neoplastic diseases or disorders.

By "hyperproliferative disease or disorder" is meant a neoplastic cell growth or proliferation, whether malignant or benign, including all transformed cells and tissues and all cancerous cells and tissues. Hyperproliferative diseases or disorders include, but are not limited to, precancerous lesions, abnormal cell growths, benign tumors, malignant tumors, and cancer. Additional nonlimiting examples of hyperproliferative diseases, disorders, and/or conditions include neoplasms, whether benign or malignant, located in the prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract.

The following examples further illustrate the invention but, of course, should not be construed as in any way limiting its scope.

Materials and Instrumentation. Gold nanoparticles (AuNPs, 83 nM) with a diameter of 5 nm were purchased from TED PELLA, INC. Prostate-specific antigen (PSA), Glucose oxidase (GOx), glucose, gold (III) chloride trihydrate ($HAuCl_4 \cdot 3H_2O$), Tween 20, fetal bovine serum (FBS), and bovine serum albumin (BSA) were purchased from Sigma-Aldrich. Tetramethylbenzidine (TMB) substrate kit, hydrogen peroxide ($H_2O_2$), bicinchoninic acid (BCA) protein assay kit, and N-Hydroxysuccinimide-activated magnetic beads (NHS-MBs) with a diameter of around 1 μm were purchased from Fisher Scientific. $H_2O_2$ Assay Kit (ab102500) was purchased from Abcam. DBCO-PEG4-NHS ester (NHS-DBCO), and Azido-PEG4-NHS ester (NHS-azide) were purchase from Click Chemistry.

Phosphate buffered saline (PBS, 10×, pH 7.4) was purchased from Mediatech, Inc. and was diluted for 10-fold when used. The 96-well polystyrene plate was purchased from R&D Systems. Monoclonal primary anti-human PSA antibody (PSA-Ab1, clone no. CHYH1), and secondary anti-human PSA antibody (PSA-Ab2, clone no. CHYH2) were purchased from Anogen/Yes Biotech Laboratory, Ltd. The serum samples were obtained from Capital Biosciences and participants have given written informed consent for scientific research. PSA (human) ELISA kit was purchased from Abnova Corporation. De-ionized water (Milli-Q grade, Millipore) with a resistivity of 18.2 MΩ-cm was used throughout this study. The UV-vis spectra of AuNP solutions were recorded with a Genesys 10 s UV-vis spectrophotometer. The absorbance of AuNP solutions in 96-well plates were collected at 530 nm by a Synergy 2 Multi-Mode Microplate Reader (Bio-Tek Instruments, Inc). TEM images were obtained by using a JEOL 1400 model at an accelerating voltage of 100 kV. Dynamic light scattering (DLS) was performed on a Zeta Sizer Nano ZS (Malvern Zetasizer 3000HS and He/Ne laser at 632.8 nm at scattering angles of 90 at 25° C.).

Example 1

This example demonstrates the identification of the AuNP-based assay.

$H_2O_2$ was first diluted with de-ionized water to result in various concentrations ranging from 10 μM to 1 mM. To the resulting $H_2O_2$ solutions was then added 0.6 mM $HAuCl_4$.

Finally, 8.3 nM AuNP seeds (5 nm in diameter) were added into each solution. The mixtures were incubated at ambient temperature for 20 min.

As the concentration of $H_2O_2$ increased, the solutions gradually turned red. The color intensity was highly associated with the concentration of $H_2O_2$. The obtained red solutions can be monitored by UV-vis spectroscopy. The absorbance at around 530 nm was intensified with increased amount of $H_2O_2$. By collecting the absorbance at 530 nm for each solution, the intensity of the red color was found to be in a linear range between 10 and 100 µM (FIG. 1), suggesting the feasibility of this probe to quantify the target of interest.

Figure 2A:
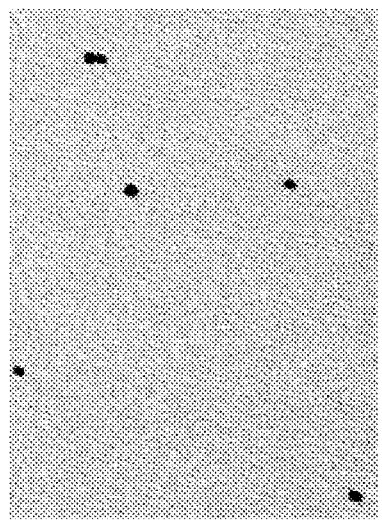
Figure 2B:
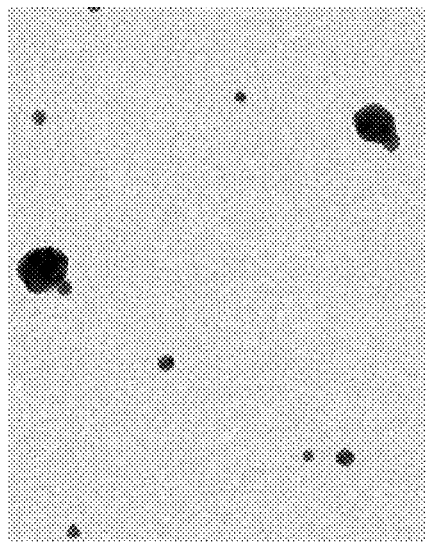
Figure 2C:
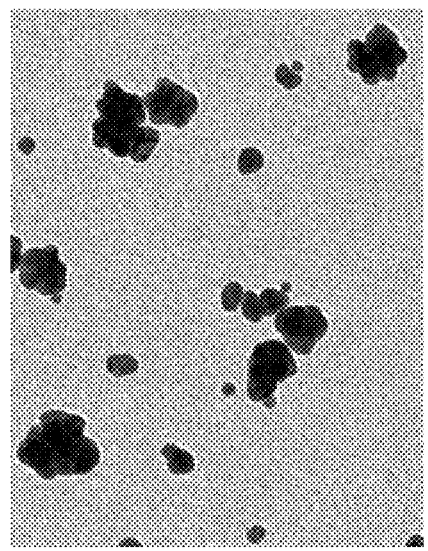
Figure 2D:
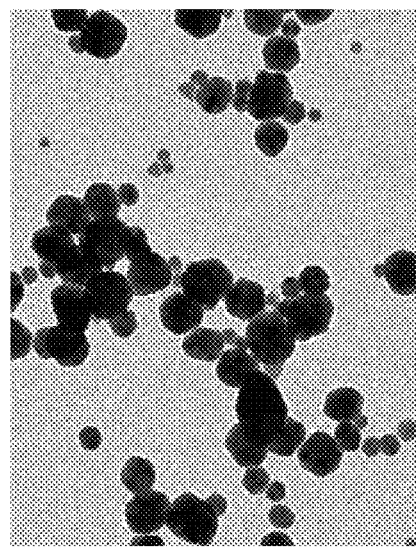
Figure 3A:
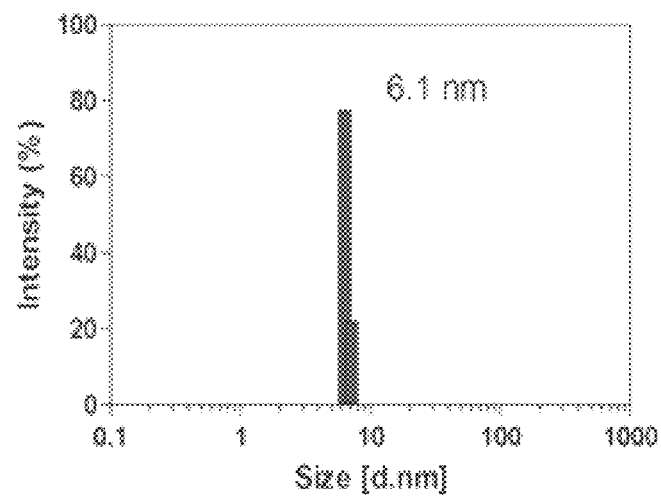
Figure 3B:
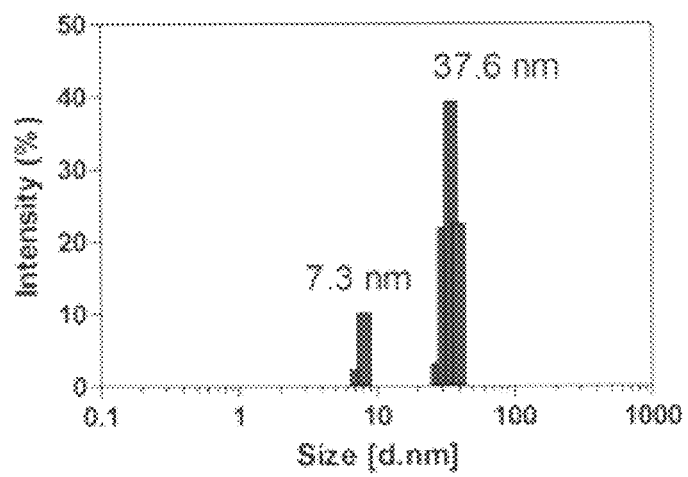
Figure 3C:
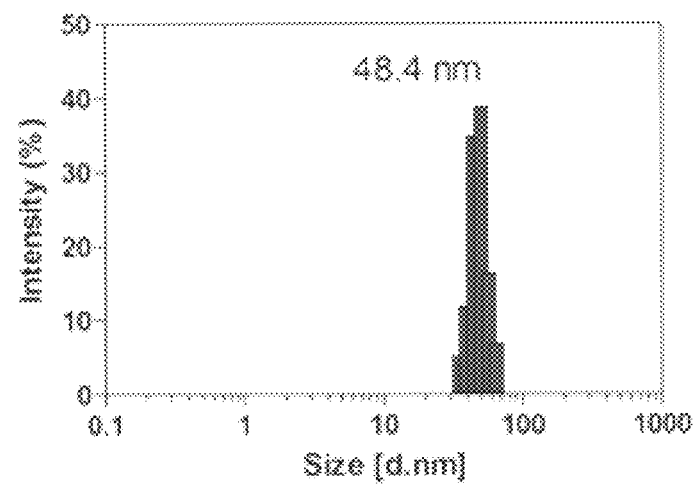
Figure 3D:
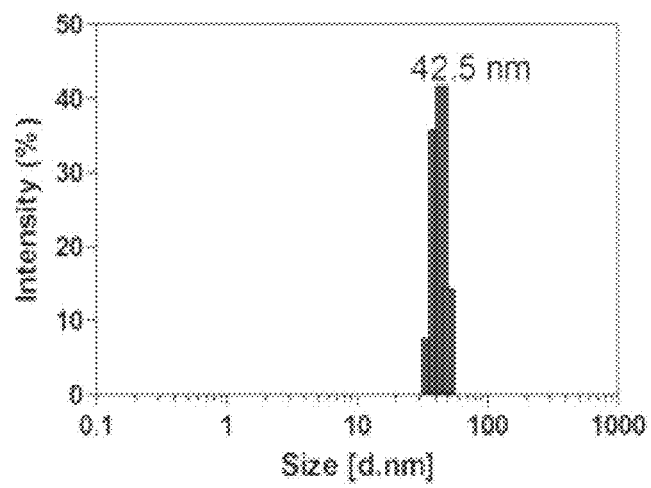

A further insight into the mechanism of the red color emergence can be obtained by transmission electron microscopy (TEM). FIG. 2A shows the TEM image of the 5 nm AuNP seeds. FIGS. 2B-D show the obtained AuNPs after treatment of the seeds with 10, 100 and 1000 µM of $H_2O_2$, respectively. For the sample treated by 10 µM of $H_2O_2$, most of AuNPs were 5 nm AuNP seeds accompanied by a few larger sized spherical AuNPs (28.4±4.6 nm in diameter). When the concentration of $H_2O_2$ was increased to 100 µM, some AuNP clusters were found, causing the enlargement of AuNPs with a wide size distribution (29.5±16.8 nm). The color of the solutions became purple most likely due to the formation of larger sized AuNPs, which was confirmed by the red shift (ca. 13 nm) of the maximum absorbance in the UV-vis spectra. It has been reported that the clusters are catalytically grown at the sharp intersections of the faces of the parent AuNP seeds. Interestingly, when the concentration of $H_2O_2$ reached 1000 µM, the clusters disappeared. Instead, the AuNPs became spherical with relatively narrow size distribution (24.5±12.2 nm). As a consequence, the color of the solutions turned red and a blue shift in the absorbance maxima was observed. The morphological change of the obtained AuNPs can be explained by the fact that Au deposit tends to smooth out the sharp edges of the particles to decrease their surface energy. The size change of the obtained AuNPs was also supported by the dynamic light scattering (DLS) analysis (FIGS. 3A-D). It is worth pointing out that other reducing agents such as ascorbic acid and NADH may have the same function as $H_2O_2$, i.e., reacting with $AuCl_4^-$ in the presence of AuNP seeds and thus causing the enlargement of AuNPs. By incubating various concentrations of ascorbic acid and NADH separately with the mixture of 5 nm AuNP seeds (8.3 nM) and $AuCl_4^-$ (0.6 mM), the color of the solutions was observed to turn red rapidly, and more reducing agents inducing more red color. The color change was reflected by the absorbance at around 530 nm.

Example 2

This example demonstrates the preparation of Ab2-GOx-MBs.

Figure 4:
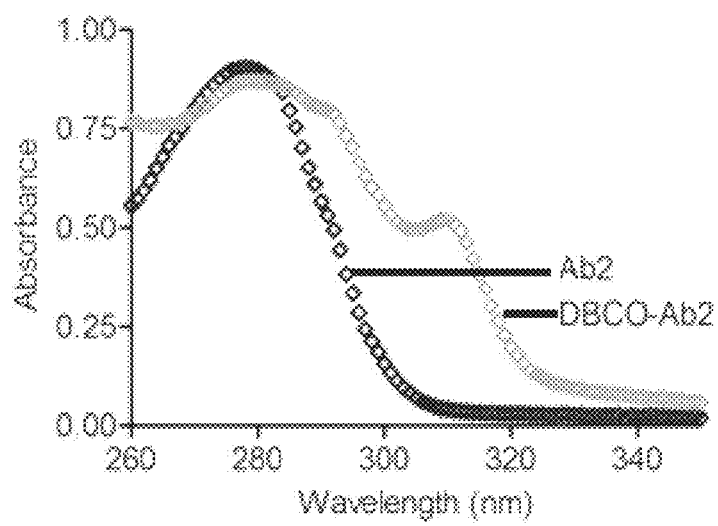
FIG. 4 depicts the UV-visible absorption spectra of purified PSA detection antibody (Ab2) and Ab2 labeled with dibenzocyclooctyl (DBCO) moieties. The absorption band at 309 nm indicates the DBCO moieties on Ab2.

To obtain Ab2-GOx-MBs, dibenzocyclooctyl (DBCO)-conjugated Ab2 was first prepared. Ab2 was dissolved in 200 µL of PBS (pH 7.4) at a concentration of 1.0 mg/mL. NHS-activated DBCO (10 mM, 6.5 µL) was then mixed with the Ab2 solution at a 50:1 mole ratio and incubated at ambient temperature for 30 min. The reaction was stopped by addition of a quenching buffer (50 mM Tris-HCl, pH 8) and the quenching reaction was allowed to proceed at ambient temperature for 5 min. The resulting products were purified using a centrifugal filter device (Amicon Ultra-0.5, Millipore) with a 30K Nominal Molecular Weight Limit (NMWL). The purified antibodies were measured by UV-vis absorption. As shown in FIG. 4, a new absorption peak at around 309 nm was observed, which was attributed to the DBCO moieties on Ab2. The number of DBCO per Ab2 can be determined from the absorbance scan of the purified product. Based on the Beer-Lambert law, $$\text{Number } DBCO \text{ per } Ab2 = \frac{A_{309}DBCO \times \varepsilon_{280}Ab2}{\varepsilon_{309}DBCO \times A_{280C}Ab2} \quad (1)$$

where $A_{309}$ DBCO is the absorbance of DBCO-Ab2 at 309 nm; $\epsilon_{309}$ DBCO and $\epsilon_{280}$ Ab2 represent the extinction coefficients of DBCO (12,000 $M^{-1}$ $cm^{-1}$) and Ab2 (204,000 respectively; $A_{280C}$ Ab2 is the corrected absorbance of DBCO-Ab2 at 280 nm, which can be calculated by the equation $A_{280C}$ $Ab2 = A_{280}$ $Ab2 - (A_{309}$ $DBCO \times CF_{DBCO})$, where $A_{280}$ Ab2 is the absorbance of DBCO-Ab2 at 280 nm; $CF_{DBCO}$ is the correction factor at 280 nm (1.089). Based on Equation 1 and FIG. 4, the average number of DBCO per Ab2 was calculated to be 21.

After obtaining DBCO-Ab2, GOx-MBs were prepared. 200 µL of NHS-activated MBs (1 mg/mL) that were 1 µM in diameter were placed into a 1.5 mL microcentrifuge tube and the supernatant was removed by a magnetic stand. Ice-cold HCl solution (1 mM) was then added to wash the beads. The activated beads were mixed with 100 µL of GOx (3 mg/mL) in PBS by votexing for 30 s. The mixture was incubated for 1 h at room temperature on a rotator. During the first 30 min of the incubation, the tube was vortexed for 15 s every 5 min. For the remaining time, the tube was vortexed for 15 s every 15 min until the reaction was complete. Once GOx-loaded MBs were obtained, the number of GOx per MB was measured to be around 76,000 by the BCA protein assay kit.

To conjugate with DBCO-Ab2, the GOx-MBs were first modified with azide groups by adding 2 µL of NHS-activated azide (1 mM) into the obtained GOx-MB solution. The resulting solution was incubated at ambient temperature for 30 min and purified by a magnetic stand. The resulting azide-modified GOx-MBs (200 µL, 1 mg/mL) were mixed with the as-prepared DBCO-Ab2 (2 µL, 1 mg/mL). The mixture was allowed to incubate at ambient temperature for 2 h. The resulting Ab2-GOx-MBs were collected and purified by a magnetic stand.

Example 3

This example demonstrates the detection of Ab2-GOx-MBs by the AuNP-based assay.

To demonstrate that Ab2-GOx-MBs can catalyze the oxidation of glucose to generate $H_2O_2$, the colorless-to-red assay was applied to monitor the generated $H_2O_2$, which in turn was used to measure the amount of Ab2-GOx-MBs. Ab2-GOx-MBs with various concentrations ranging from $10^5$ to $10^9$ particles/mL were incubated with glucose (5 mM) in pH 5.0 citrate-$Na_2HPO_4$ buffered solutions to produce various amounts of $H_2O_2$. The resulting solutions were then incubated at 35° C. for 10 min. The obtained solutions were added to the mixture of 5 nm AuNP seeds (8.3 nM) and $AuCl_4^-$ (0.6 mM). The mixtures were then incubated at ambient temperature for 20 min. The absorbance at 530 nm was recorded by a Synergy 2 Multi-Mode Microplate Reader.

Figure 5:
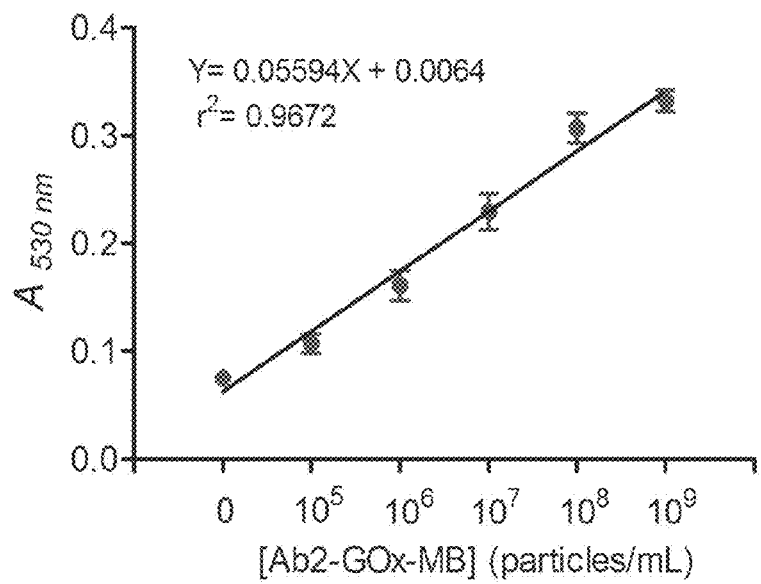
FIG. 5 depicts the detection of the colorless-to-red assay for various concentrations of Ab2-GOx-MB ranging from $10^5$ to $10^9$ particles/mL. Error bars show the standard deviations of three independent measurements.

Under the optimized reaction conditions of pH 5 and a temperature of 35° C., it was observed that the solutions turned red gradually, and the color intensity is highly related to the concentration of Ab2-GOx-MBs, which was further confirmed by the absorbance at 530 nm (FIG. 5). On the basis of a signal-to-noise ratio of 3, the limit of detection (LOD) of the colorless-to-red probe for Ab2-GOx-MBs was determined to be $3.4 \times 10^4$ particles/mL with a wide linear range from $10^5$ to $10^9$ particles/mL.

Example 4

This example demonstrates the procedure of AuNP-based immunoassay for PSA.

The immunoassay detection was performed in 96-well polystyrene (PS) plates. Firstly, Ab1 (4 µg/mL) in bicarbonate buffer (100 mM, pH 9.6) was added into the wells in the PS plate and incubated at 4° C. overnight. After rinsing with PBS for 3 runs, 1% bovine serum albumin (BSA) in PBS was added into each well as blocking agent. Then, PSA-spiked PBS and 100% fetal bovine serum solutions were added respectively at concentrations ranging from 10 to $10^5$ fg/mL, and the PBS-only and serum-only solutions were set as controls. To test the possible interference from the unknown matrices in real samples, PSA was also spiked into fetal bovine sera at the same concentrations as another group. The plate was kept at 37° C. for 1 h and washed with PBS for 3 runs. Later, 100 µL of Ab2-GOx-MB (0.1 mg/mL) solutions were added into each well, and incubated for 30 min. 200 µL of PBST was added into each well and rinsed for 3 runs. Glucose (5 mM) in pH 5.0 citrate-$Na_2HPO_4$ buffered solutions was added into each well and incubated at 35° C. for 10 min. To each well was added the mixture of 5 nm AuNP seeds (8.3 nM) and $AuCl_4^-$ (0.6 mM). The mixtures were incubated at ambient temperature for 20 min. In the end, photographs were taken and their corresponding absorbance at 530 nm was recorded by a Synergy 2 Multi-Mode Microplate Reader.

Figure 6:
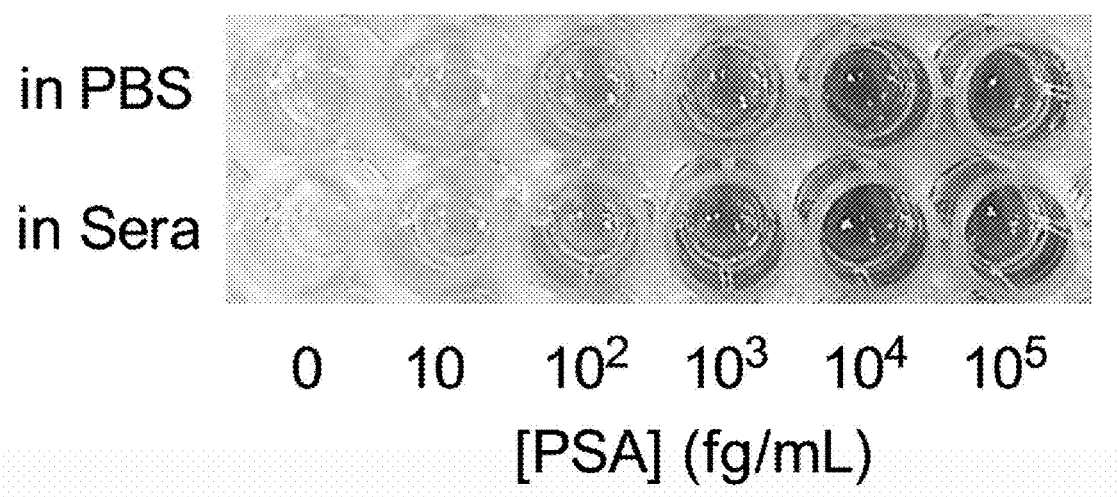
FIG. 6 depicts the naked eye detection of PSA with different concentrations in PBS and fetal bovine sera.

For both groups of PSA-spiked samples, the colorless solutions became purple, whose intensity is highly dependent on the concentration of PSA. Higher concentrations of PSA enabled more purple color (FIG. 6). In comparison, the samples remained colorless if no PSA was added. More importantly, the tendency in color emergence of the two groups of samples is almost the same, indicating that the unrelated components in clinical samples may have negligible effects on this immunoassay. Therefore, the emergence of purple color is due to the biospecific interactions between PSA and its antibodies rather than the nonspecific adsorption of Ab2-GOx-MB on the PS substrate. The lowest detectable concentration of PSA where the purple color can be clearly discriminated by the naked eye was 10 fg/mL (300 aM). Note that the color of the solution is purple rather than red. This phenomenon is most likely due to the fact that the amount of the generated $H_2O_2$ is not sufficient to catalyze the formation of uniform spherical AuNPs. To test this hypothesis, the concentration of the generated $H_2O_2$ was measured in each well. The amount of the generated $H_2O_2$ is highly correlated with the PSA concentration. More PSA can pull down more Ab2-GOx-MB on the PS substrate, thus inducing more $H_2O_2$. Owing to the fact that all the samples generated less than 100 mM of $H_2O_2$, in which larger sized AuNP clusters were formed, leading to purple colored solution, which agreed well with the results in FIG. 2.

Furthermore, the naked-eye results were validated by measuring the absorbance at 530 nm on a conventional microplate reader. The calibration curves suggested that the linear detection ranges for both cases are from 10 to $10^5$ fg/mL. This linear range is much wider than that of HRP-based ELISA, indicating that the inventive immunoassay is particularly useful for quantitative detection of biomarkers whose concentrations are from fg/mL to pg/mL. For the spiked PSA in PBS, the LOD defined by a signal-to-noise ratio of 3 was determined to be 3.1 fg/mL (93 aM), while that for PSA spiked in sera was 4.6 fg/mL (138 aM). By contrast, the LOD of HRP-based ELISA for PSA in sera was 0.21 ng/mL (6.3 pM), at least 4 orders of magnitude higher than that of the AuNP-based immunoassay.

The excellent detection sensitivity can be attributed to two rounds of signal amplification. In the first round, MBs are used to load many thousands of GOx, which are then conjugated with detection antibodies via copper-free click chemistry. It is understandable that more GOx can generate more $H_2O_2$, thus producing more Au(0). In the second round, the activity of the loaded GOx is highly maintained, and the anchored GOx can catalyze its substrate glucose oxidase to generate $H_2O_2$. $H_2O_2$ can react with $AuCl_4^-$ in the presence of 5 nm AuNP seeds and thus causes the enlargement of AuNPs, whose extinction coefficients ($10^8$-$10^{10}$ M $cm^{-1}$) are much higher than those of organic dyes. This Au growth event can be reflected by the color emergence of the AuNP solutions from colorless to purple, which can be observed by the naked eye. Very small amount of the analyte can thus be detected because of the high density of GOx on MB and the Au growth reaction.

Figure 7:
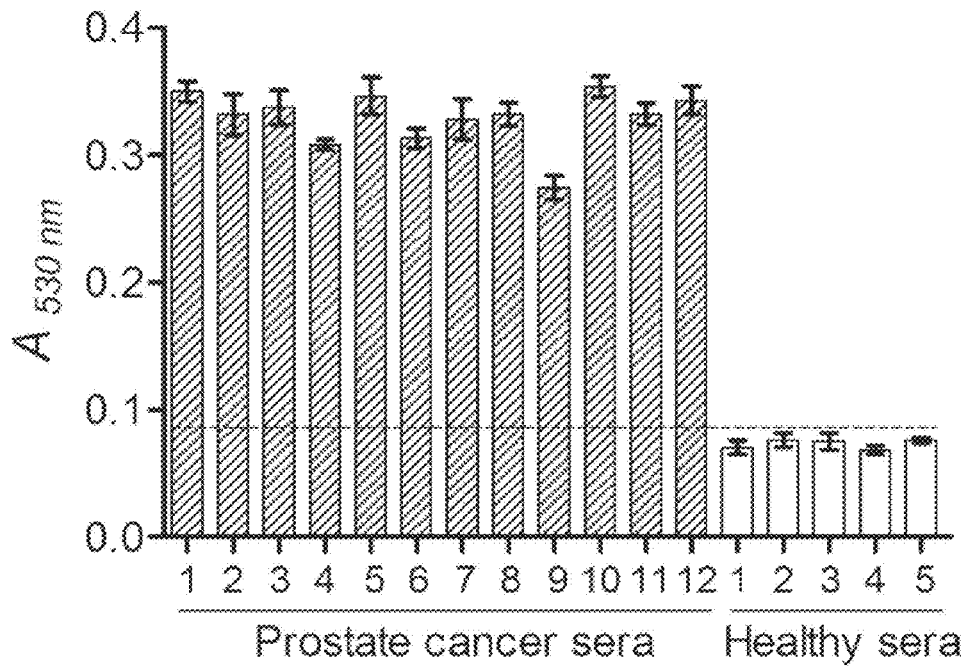
FIG. 7 depicts that detection of PSA in human sera using the gold nanoparticle-based quantitative immunoassay.
Figure 8:
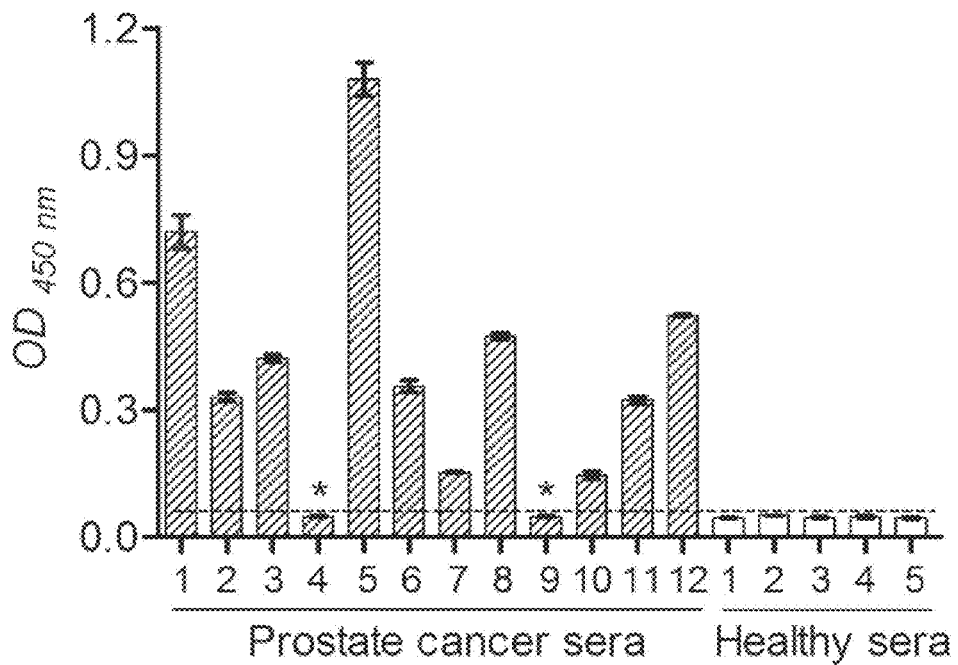
FIG. 8 depicts that detection of PSA in human sera using conventional HRP-based ELISA.

Encouraged by the unprecedented sensitivity and wide linear detection range for PSA, 12 patient sera with prostate cancer and 5 healthy sera were employed to evaluate the capability of the assay of the invention in the real world. The results were compared with the HRP-based ELISA. The differentiation of positive and negative signals depended on the clinical threshold which was indicated by the horizontal dotted line. As shown in FIG. 7, all 12 patient sera were positively detected by the AuNP-based immunoassay; that is, the $A_{530\,nm}$ values are clearly above the clinical threshold which was set to be 0.085. Meanwhile, the signals for the 5 healthy samples were below the clinical threshold, indicating that the AuNP-based immunoassay provides 100% sensitivity and 100% specificity for PSA. In comparison, two patient sera (Nos. 4 and 9) were not positively detected by HRP-based ELISA (FIG. 8); that is, the $OD_{450\,nm}$ values were below the clinical threshold (where the $OD_{450\,nm}$ value is 0.05). The results are not surprising because of the moderate sensitivity of HRP-based ELISA, which may not reach the clinical concentrations of PSA in certain patient sera (generally below 0.1 ng/mL).

Figure 9:
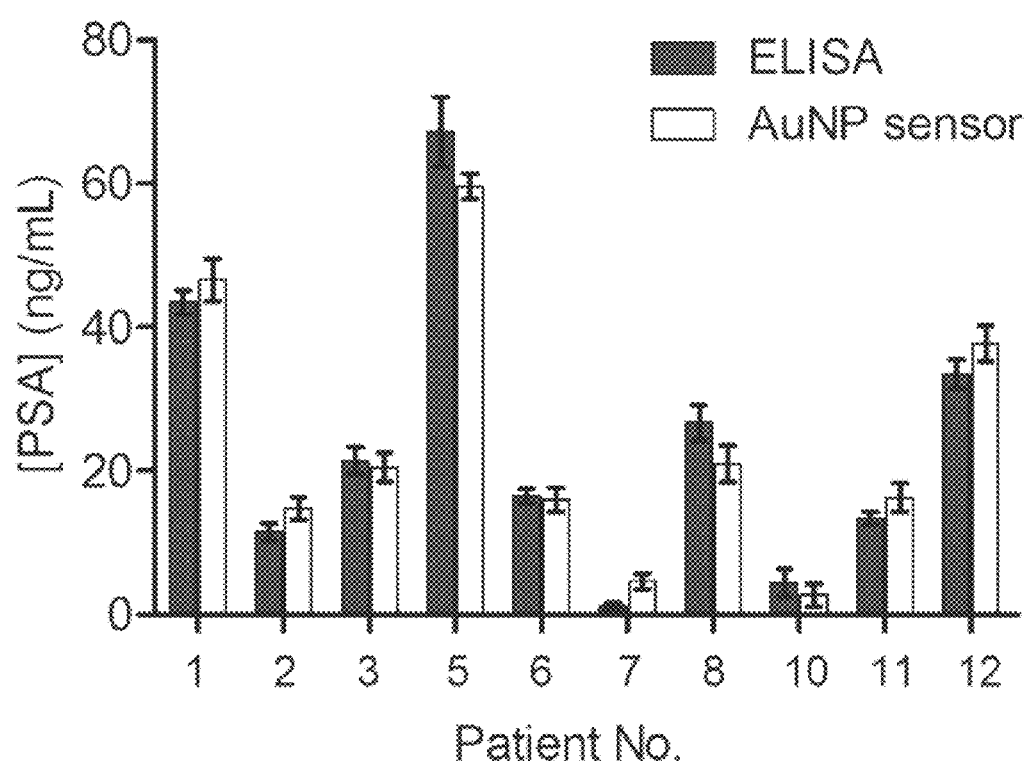
FIG. 9 depicts the results of the quantitative detection of PSA in clinical samples by the gold nanoparticle-based immunoassay compared with HRP-based ELISA.

To demonstrate that the AuNP-based immunoassay can accurately quantify target molecules in biological samples, the patient sera samples were diluted using fetal bovine serum by 10,000-fold to correspond to the linear range of the calibration curve. As a comparison, the undiluted patient sera were also screened by HRP-based ELISA. Results from the two methods showed excellent correlation, and no significant difference in quantifying the amounts of PSA was observed ($P>0.05$) (FIG. 9). On the basis of the calibration curve, the PSA concentrations in patient Nos. 4 and 9 that were undetectable by HRP-based ELISA were determined to be 0.031 and 0.0056 ng/mL respectively by the AuNP-based immunoassay. These results indicate that the AuNP-based immunoassay not only can be used for the identification of very low concentrations of cancer protein biomarkers in clinical samples by the naked eye, but also can quantitatively measure the biomarkers in a wide linear range.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for detecting the presence or absence of a prostate specific antigen ("PSA") in a biological sample comprising the steps of:
   (a) contacting the biological sample with a capture binding sequence immobilized on a surface, wherein the capture binding sequence is a monoclonal primary anti-human PSA antibody,
   (b) providing nanoparticles having a detection binding sequence and glucose oxidase conjugated thereto, wherein the detection binding sequence is a secondary anti-human PSA antibody,
   (c) contacting the surface with the nanoparticles,
   (d) separating any unbound nanoparticles from the surface,
   (e) incubating the resulting surface with a glucose solution and a mixture comprising gold nanoparticles and a gold salt, wherein the gold nanoparticles have an initial particle size of about 5 nm, and
   (f) observing a change in absorbance of visible light at a wavelength of approximately 530 nm,
wherein a lower level of detection of the method is 10 fg/mL of PSA.

2. The method of claim 1, wherein the detection binding sequence is a dibenzocyclooctyl-conjugated binding sequence.

3. The method of claim 1, wherein the gold nanoparticles are present in a concentration of about 10 nM or less.

4. The method of claim 1, wherein the observing is performed visually or spectrophotometrically.

5. The method of claim 1, wherein the biological sample is selected from urine, blood, serum, and biopsy tissue.

6. The method of claim 1, wherein the PSA is present in the biological sample at a concentration of about 10 fg/mL to about $10^5$ fg/mL.

7. A method for diagnosing the presence of a prostate specific antigen ("PSA") in a subject comprising the steps of:
   (a) contacting a biological sample obtained from the subject with a capture antibody immobilized on a surface, wherein the capture antibody is a monoclonal primary anti-human PSA antibody,
   (b) providing magnetic beads having a detection antibody and glucose oxidase conjugated thereto, wherein the detection antibody is a secondary anti-human PSA antibody,
   (c) contacting the surface with the magnetic beads,
   (d) separating any unbound magnetic beads from the surface,
   (e) incubating the resulting surface with a glucose solution and a mixture comprising gold nanoparticles and a gold salt, wherein the gold nanoparticles have an initial particle size of about 5 nm, and
   (f) observing a change in absorbance of visible light at a wavelength of approximately 530 nm,
wherein a lower level of detection of the method is about 10 fg/mL of PSA.

8. The method of claim 7, wherein the detection antibody is a dibenzocyclooctyl-conjugated antibody.

9. The method of claim 7, wherein the gold nanoparticles are present in a concentration of about 10 nM or less.

10. The method of claim 7, wherein the observing is performed visually or spectrophotometrically.

11. The method of claim 7, wherein the biological sample is selected from urine, blood, serum, and biopsy tissue.

12. A method for diagnosing the presence of a prostate specific antigen ("PSA") in a subject comprising the steps of:
   (a) contacting a biological sample obtained from the subject with a capture antibody, wherein the capture antibody is a mouse monoclonal antibody to human prostate specific antigen, and which antibody is the CHYH1 clone, wherein the capture antibody is immobilized on a polystyrene surface,
   (b) providing magnetic beads having a detection antibody and glucose oxidase conjugated thereto, wherein the detection antibody is a mouse monoclonal antibody to human prostate specific antigen, and which antibody is the CHYH2 clone,
   (c) contacting the surface with the magnetic beads,
   (d) separating any unbound magnetic beads from the surface,
   (e) incubating the resulting surface with a glucose solution and an aqueous mixture comprising gold nanoparticles and gold (III) chloride trihydrate, wherein the gold nanoparticles have an initial particle size of about 5 nm, and (f) observing a change in absorbance of visible light at a wavelength of approximately 530 nm,
wherein a lower level of detection of the method is about 10 fg/mL of PSA.

* * * * *